US010655362B2

(12) United States Patent
Ulleberg

(10) Patent No.: US 10,655,362 B2
(45) Date of Patent: May 19, 2020

(54) BREATHALYZER CAR KEY LOCKING DEVICE

(71) Applicant: LockedUp Group, LLC, Blue Springs, MO (US)

(72) Inventor: Eric Ulleberg, Blue Springs, MO (US)

(73) Assignee: LockedUp Group, LLC, Blue Springs, MO (US)

( * ) Notice: Subject to any disclaimer, the term of this patent is extended or adjusted under 35 U.S.C. 154(b) by 0 days.

(21) Appl. No.: 16/534,235

(22) Filed: Aug. 7, 2019

(65) Prior Publication Data

US 2020/0048937 A1 Feb. 13, 2020

Related U.S. Application Data

(60) Provisional application No. 62/717,361, filed on Aug. 10, 2018.

(51) Int. Cl.
| | |
|---|---|
| *E05B 19/00* | (2006.01) |
| *E05B 73/00* | (2006.01) |
| *E05B 13/00* | (2006.01) |
| *G07C 9/00* | (2020.01) |
| *G01N 33/497* | (2006.01) |
| *H05K 9/00* | (2006.01) |
| *B60K 28/06* | (2006.01) |
| *E05B 47/00* | (2006.01) |

(52) U.S. Cl.
CPC .......... *E05B 19/0005* (2013.01); *E05B 13/00* (2013.01); *E05B 19/0082* (2013.01); *E05B 73/00* (2013.01); *G01N 33/4972* (2013.01); *G07C 9/00571* (2013.01); *H05K 9/0045* (2013.01); *B60K 28/063* (2013.01); *E05B 2047/0092* (2013.01)

(58) Field of Classification Search
CPC ............ E05B 19/0005; E05B 19/0082; E05B 19/0094; E05B 2047/0092; H05K 9/0045; H05K 9/0081
See application file for complete search history.

(56) References Cited

U.S. PATENT DOCUMENTS 5,274,550 A * 12/1993 Greenlee ............... G06F 15/025
73/23.3
6,819,248 B2 * 11/2004 Gotfried ............... B60R 25/104
340/573.1

(Continued)

*Primary Examiner* — Christopher J Boswell
(74) *Attorney, Agent, or Firm* — Hovey Williams LLP

(57) ABSTRACT

A breathalyzer car key locking device comprises a mouthpiece, an alcohol sensor, a locking mechanism, and a processing element. The mouthpiece receives breath from a user. The alcohol sensor receives the user's breath from the mouthpiece, determines a blood alcohol level of the breath, and outputs an electronic blood alcohol level signal whose voltage level or digital data value varies according to the determined blood alcohol level. The locking mechanism exists in one of two states including a locked state and an unlocked state. The locking mechanism retains a car key in the locked state and releases the car key in the unlocked state. The processing element receives the blood alcohol level signal from the alcohol sensor, and transmits an electronic locking signal that places the locking mechanism in the locked state when an aspect of the blood alcohol level signal is greater than or equal to a predetermined threshold.

20 Claims, 4 Drawing Sheets

(56) References Cited

U.S. PATENT DOCUMENTS

| | | | | |
|---|---|---|---|---|
| 7,934,577 | B2* | 5/2011 | Walter | B60K 28/063 |
| | | | | 180/272 |
| 7,949,541 | B2* | 5/2011 | McGinn | G06Q 30/02 |
| | | | | 705/1.1 |
| 8,049,631 | B1* | 11/2011 | Edwards | B60K 28/063 |
| | | | | 340/426.13 |
| 8,359,901 | B2* | 1/2013 | Freund | G07C 5/0891 |
| | | | | 73/23.3 |
| 9,404,286 | B2* | 8/2016 | Stevens | E05B 17/223 |
| 2004/0085187 | A1* | 5/2004 | Gotfried | G07C 9/00896 |
| | | | | 340/5.52 |
| 2006/0180378 | A1* | 8/2006 | Nordin | B60K 28/063 |
| | | | | 180/272 |
| 2006/0182661 | A1* | 8/2006 | Aquila | B60K 28/063 |
| | | | | 422/84 |
| 2006/0253711 | A1* | 11/2006 | Kallmann | B60K 28/063 |
| | | | | 713/186 |

* cited by examiner

BREATHALYZER CAR KEY LOCKING DEVICE

RELATED APPLICATION

The current patent application is a utility patent application which claims priority benefit, with regard to all common subject matter, to U.S. Provisional Patent Application No. 62/717,361, filed Aug. 10, 2018, and entitled "PORTABLE BREATHALYZER WITH A CAR KEY LOCKING MECHANISM". The earlier-filed provisional application is hereby incorporated by reference into the current patent application in its entirety.

FIELD

Embodiments of the current invention relate to breathalyzer devices that include a mechanism to retain a car key.

DESCRIPTION

Breathalyzer devices provide a measurement of a person's blood alcohol level. They are often used by law enforcement to catch people who have been drinking and driving. While these devices may be effective at measuring blood alcohol level, they do nothing to prevent a person with a blood alcohol level above a legal threshold from driving a car anyway.

SUMMARY

Embodiments of the current invention provide a breathalyzer car key locking device which retains and holds a driver's car key, but will not release the car key until the driver has successfully passed a breathalyzer breath analysis test. The breathalyzer car key locking device broadly comprises a housing, a mouthpiece, an alcohol sensor, a locking mechanism, and a processing element. The housing includes a plurality of walls connected to one another to form a box with an internal cavity. The mouthpiece is coupled to the housing and configured to receive breath from a user. The alcohol sensor is positioned in the internal cavity and configured to receive the user's breath from the mouthpiece, determine a blood alcohol level of the breath, and output an electronic blood alcohol level signal whose voltage level or digital data value varies according to the determined blood alcohol level. The locking mechanism is positioned in the internal cavity and exists in one of two states including a locked state and an unlocked state. The locking mechanism is configured to retain a car key in the locked state and release the car key in the unlocked state. The processing element is configured or programmed to receive the blood alcohol level signal from the alcohol sensor, and transmit an electronic locking signal to the locking mechanism that places the locking mechanism in the locked state when the voltage level or digital data value of the blood alcohol level signal is greater than or equal to a predetermined threshold and places the locking mechanism in the unlocked state when the voltage level or digital data value of the blood alcohol level signal is less than the threshold.

Another embodiment of the provides a breathalyzer car key locking device broadly comprising a housing, a mouthpiece, an alcohol sensor, a locking mechanism, a car key slot, and a processing element. The housing includes a plurality of walls connected to one another to form a box with an internal cavity. The mouthpiece is coupled to the housing and configured to receive breath from a user. The alcohol sensor is positioned in the internal cavity and configured to receive the user's breath from the mouthpiece, determine a blood alcohol level of the breath, and output an electronic blood alcohol level signal whose voltage level or digital data value varies according to the determined blood alcohol level. The locking mechanism is positioned in the internal cavity and exists in one of two states including a locked state and an unlocked state. The locking mechanism includes a solenoid with a plunger configured to extend from the solenoid when in the locked state and retract into the solenoid when in the unlocked state. The car key slot is accessed through an opening in a wall of the housing and is configured to receive the car key. The car key slot includes a plurality of walls connected to one another to form an open-ended box, with one of the walls including an opening which receives the plunger such that the plunger contacts the car key to retain the car key when in the locked state and does not contact the car key to release the car key when in the unlocked state. The processing element is configured or programmed to receive the blood alcohol level signal from the alcohol sensor, and transmit an electronic locking signal to the locking mechanism that places the locking mechanism in the locked state when the voltage level or digital data value of the blood alcohol level signal is greater than or equal to a predetermined threshold and places the locking mechanism in the unlocked state when the voltage level or digital data value of the blood alcohol level signal is less than the threshold.

Yet another embodiment of the provides a breathalyzer car key locking device broadly comprising a housing, a mouthpiece, an alcohol sensor, a car key chamber, a locking mechanism, and a processing element. The housing includes a plurality of walls connected to one another to form a box with an internal cavity. The mouthpiece is coupled to the housing and configured to receive breath from a user. The alcohol sensor is positioned in the internal cavity and configured to receive the user's breath from the mouthpiece, determine a blood alcohol level of the breath, and output an electronic blood alcohol level signal whose voltage level or digital data value varies according to the determined blood alcohol level. The car key chamber is positioned in the internal cavity and configured to retain a car key. The car key chamber exists in one of two states including an open state and a closed state. The locking mechanism is positioned in the internal cavity and existing in one of two states including a locked state and an unlocked state. The locking mechanism is configured to prevent access to the car key chamber in the locked state and allow access to the car key chamber in the unlocked state. The processing element is configured or programmed to receive the blood alcohol level signal from the alcohol sensor, and transmit an electronic locking signal to the locking mechanism that places the locking mechanism in the locked state when the voltage level or digital data value of the blood alcohol level signal is greater than or equal to a predetermined threshold and places the locking mechanism in the unlocked state when the voltage level or digital data value of the blood alcohol level signal is less than the threshold.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein.

Figure 1:
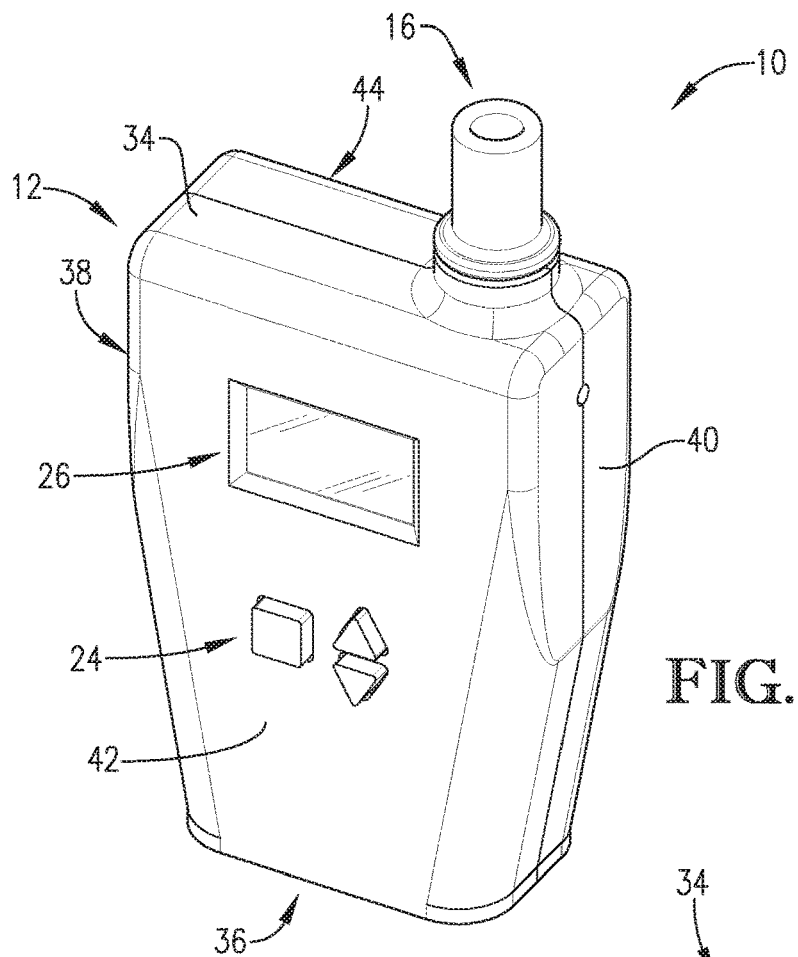
FIG. 1 is a top perspective view of a breathalyzer car key locking device, constructed in accordance with at least a first embodiment of the current invention, the breathalyzer car key locking device including a housing, a mouthpiece, a user interface, and a display shown in the figure.
Figure 2:
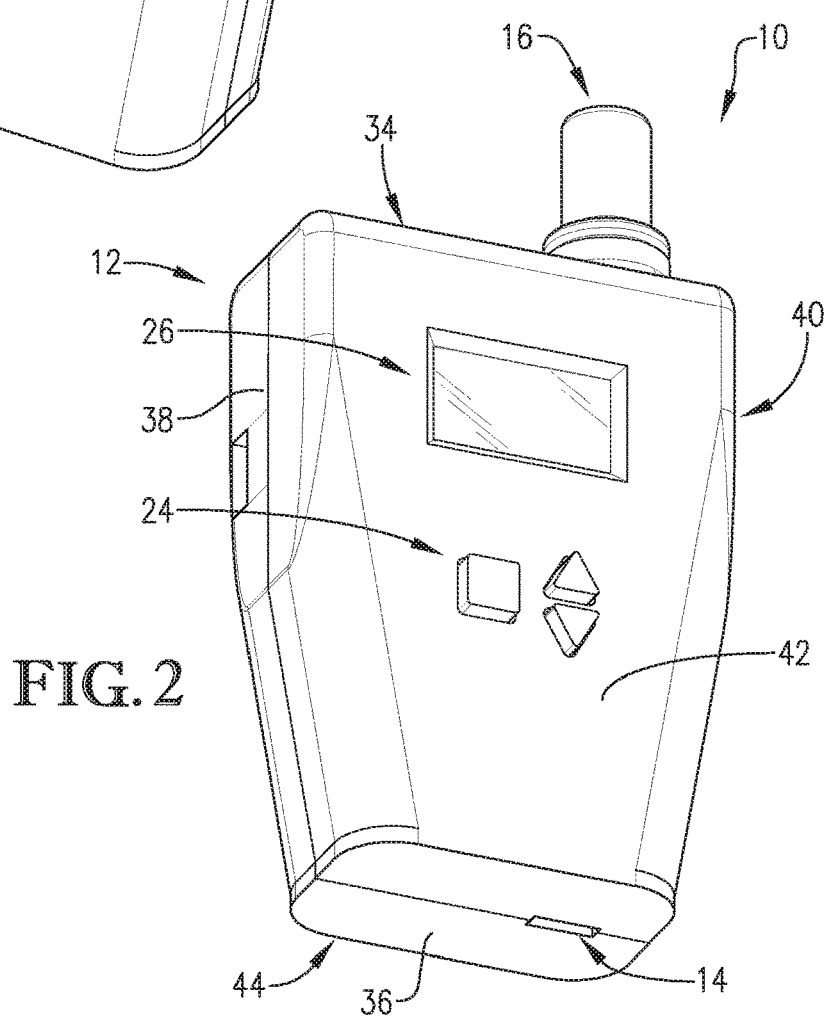
FIG. 2 is a bottom perspective view of the breathalyzer car key locking device further including a car key slot shown in the figure.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

A portable breathalyzer car key locking device 10, constructed in accordance with various embodiments of the current invention, is shown in FIGS. 1-6. The breathalyzer car key locking device 10 broadly comprises a housing 12, a car key slot 14, a mouthpiece 16, an alcohol sensor 18, a locking mechanism 20, a key detector 22, a user interface 24, a display 26, a communication element 28, and a processing element 30. The breathalyzer car key locking device 10 is utilized to retain a car key 32 while a user consumes alcohol. The breathalyzer car key locking device 10 releases the car key 32 only when the user has a blood alcohol level that is below a threshold. Typically, the car key 32 is formed from a metal or metal alloy and includes a handle and a blade. In some embodiments, the handle may be coated or covered with a plastic.

The housing 12 retains the other components of the breathalyzer car key locking mechanism 20. The housing 12 may include a top wall 34, a bottom wall 36, a left side wall 38, a right side wall 40, a front wall 42, and a back wall 44 rigidly connected to one another to form a generally rectangular box shape, although other shapes are possible. In various embodiments, some walls 34, 36, 38, 40, 42, 44 may be molded to one another. The walls 34, 36, 38, 40, 42, 44 may be planar or may include contours, tapers, or other non-planar features. In addition, some walls may include one or more openings. The walls 34, 36, 38, 40, 42, 44 may be formed from rigid or hardened materials such as plastics, metals, or metal alloys. The housing 12 may further include an internal cavity, whose extents are defined by the walls 34, 36, 38, 40, 42, 44.

Figure 3:
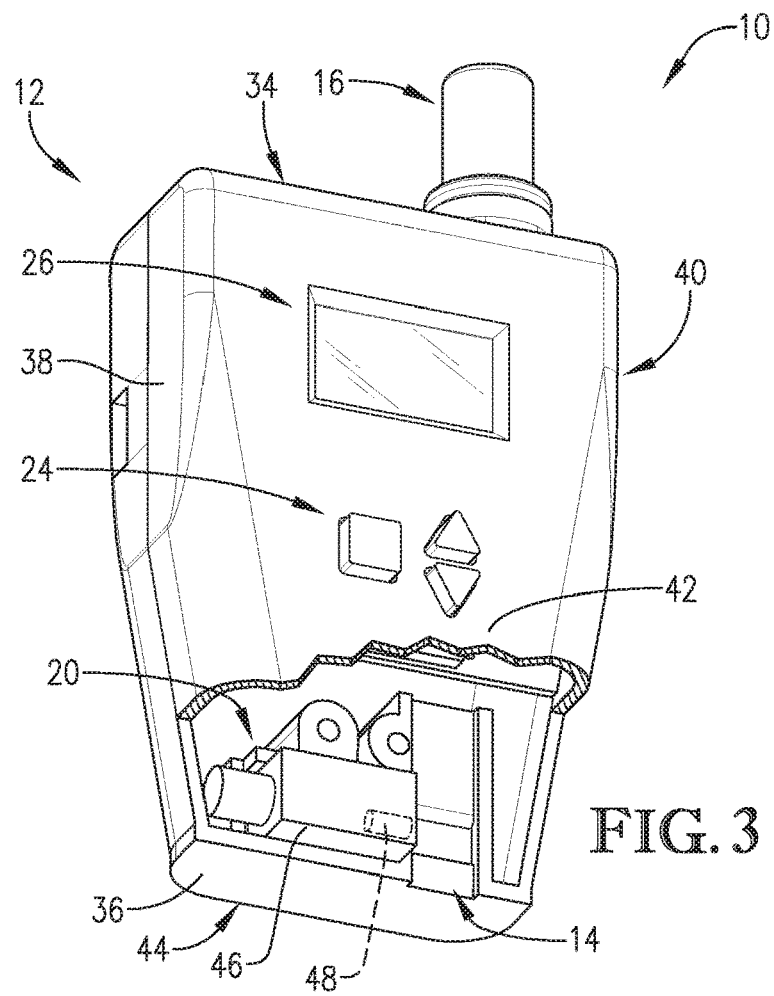
FIG. 3 is a bottom perspective view of the breathalyzer car key locking device with a portion of the housing cut away to reveal more of the car key slot and a locking mechanism which interfaces with the car key slot.
Figure 4:
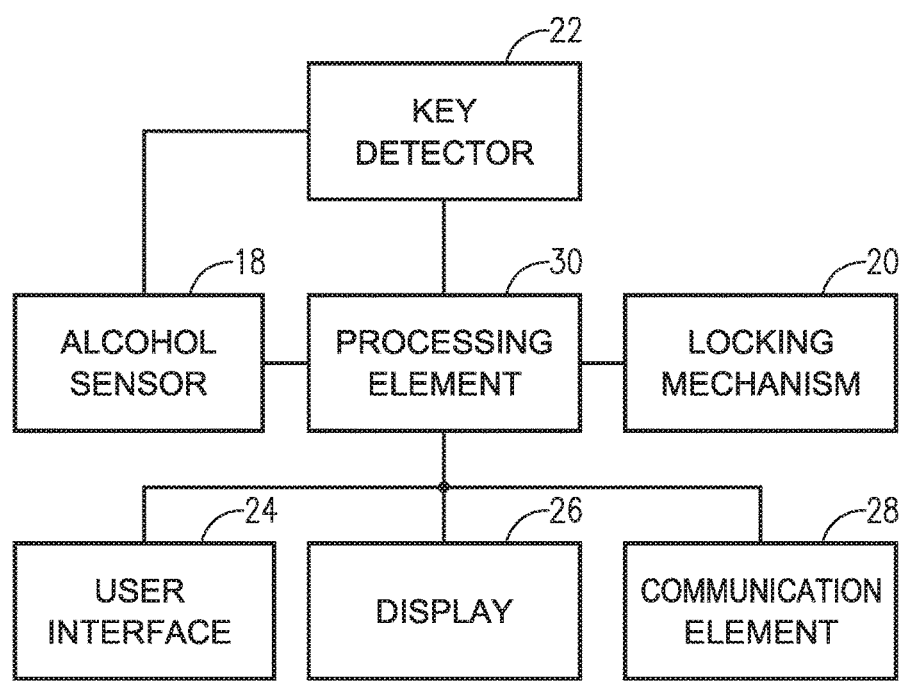
FIG. 4 is a schematic block diagram of various electronic components of the breathalyzer car key locking device.
Figure 5:
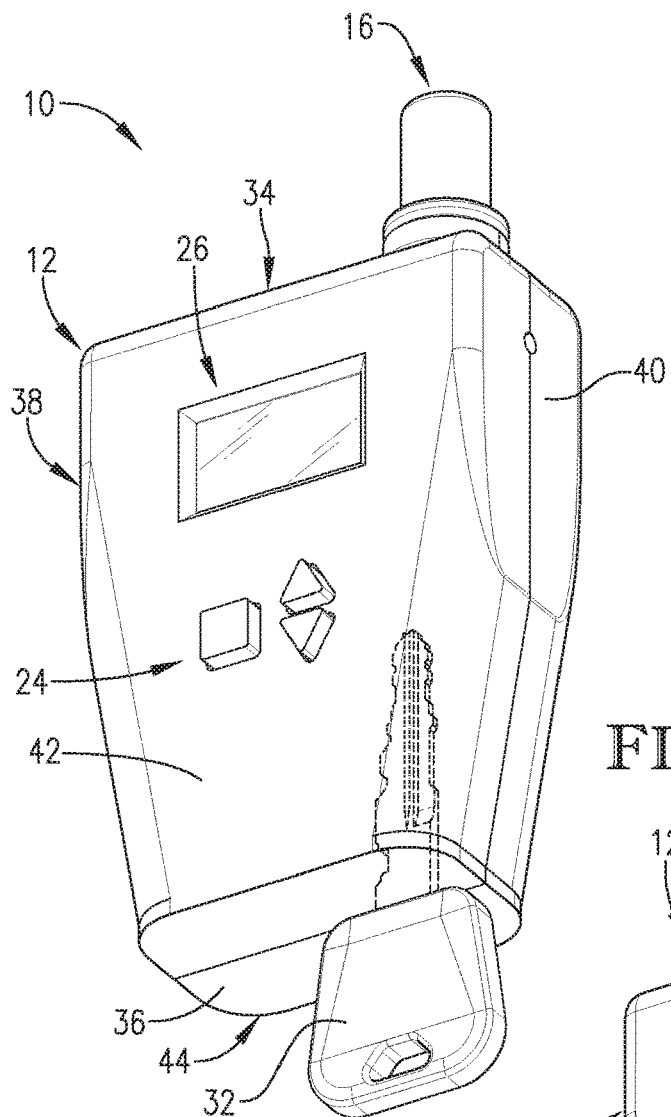
FIG. 5 is a bottom perspective view of the breathalyzer car key locking device illustrating a car key inserted into the car key slot.
Figure 6:
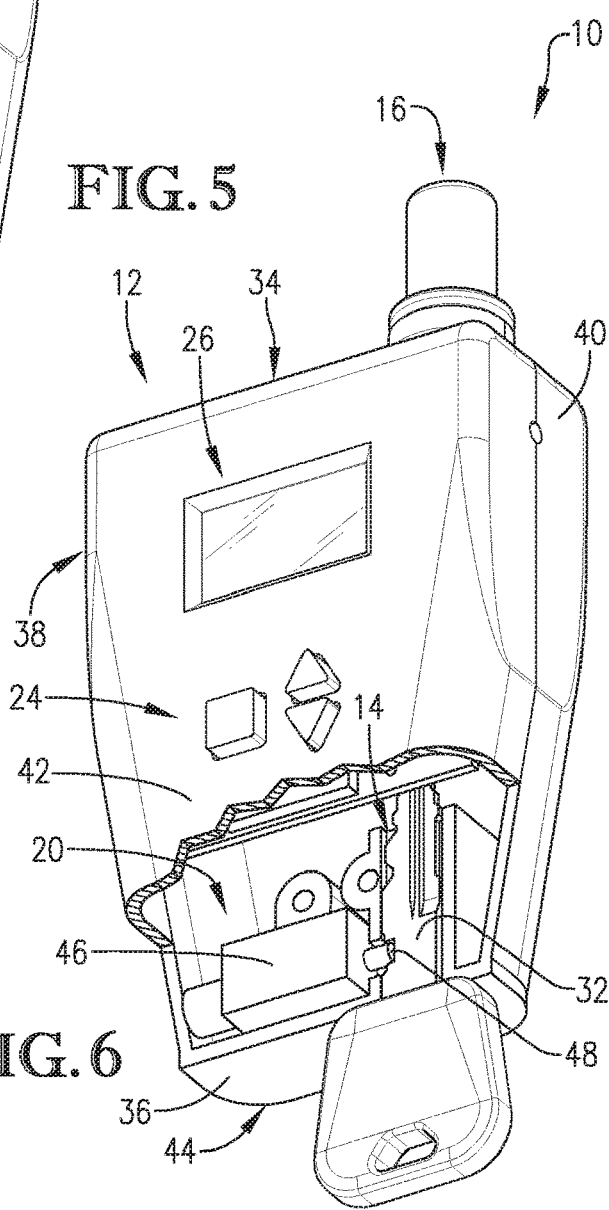
FIG. 6 is a bottom perspective view of the breathalyzer car key locking device with a portion of the housing cut away to reveal the locking mechanism retaining the car key.

The car key slot 14, as shown in FIGS. 3 and 6, provides a space in which the car key 32 is held while it is retained by the locking mechanism 20. The car key slot 14 includes four side walls connected to one another to form a box with a generally rectangular cross-sectional shape with a cross-sectional area that is big enough to retain an average car key 32. First and second opposing ends of the car key slot 14 may be open. The first end of the car key slot 14 aligns with an opening on the bottom wall 36 of the housing 12. The car key slot 14 includes an opening along one of the side walls for the locking mechanism 20 to access the car key 32, as described in more detail below.

The mouthpiece 16 generally has a tubular shape and includes a single circumferential side wall with a first end and an opposing second end. Alternatively, the mouthpiece 16 may have a rectangular cross-sectional shape with four side walls connected to one another and having a hollow interior. The user breathes into the first end of the mouthpiece 16. Thus, the first end of the mouthpiece 16 may have rounded or smooth edges. The second end of the mouthpiece 16 is coupled to an opening on the top wall 34 of the housing 12.

The alcohol sensor 18 generally measures or detects a level, or content, of alcohol, particularly ethanol, that is present in the gas that surrounds the alcohol sensor 18. The alcohol sensor 18 may be formed from active and passive electronic circuits and/or devices. In some embodiments, the alcohol sensor 18 may also include, or be in electronic communication with, electronic components, such as a capacitor, to provide necessary power and heat for the alcohol sensor 18 to a blood alcohol level. The alcohol sensor 18 outputs an electronic alcohol level signal with a characteristic that varies according to the amount of alcohol detected, that is a blood alcohol level, or blood alcohol content. For example, the alcohol level signal may include an analog voltage whose level varies according to the amount of alcohol detected, wherein a greater amount of alcohol surrounding the alcohol sensor 18 results in a higher level of the analog voltage output, and a lesser amount of alcohol surrounding the alcohol sensor 18 results in a lower level of the analog voltage output. Additionally, or alternatively, the alcohol level signal may include digital data whose value varies according to the amount of alcohol detected, wherein a greater amount of alcohol surrounding the alcohol sensor 18 results in a higher value of the digital data output, and a lesser amount of alcohol surrounding the alcohol sensor 18 results in a lower value of the digital data output. The alcohol sensor 18 may be positioned within the mouthpiece 16 near the second end or within the internal cavity of the housing 12 adjacent to the second end of the mouthpiece 16.

The device 10 may include additionally, or alternatively, one or more sensors to detect the user's inhaling of, or exposure to, marijuana smoke or the user's ingesting of tetrahydrocannabinol (THC). The sensors may be able to test blood, saliva, or urine in order to detect the presence of marijuana or THC markers in the user's body. The sensors may output an electronic signal with an electrical characteristic, or digital data, that varies according to the amount of the markers detected.

The locking mechanism 20 generally retains the car key 32 while the user is consuming alcohol. Exemplary embodiments of the locking mechanism 20 may include a solenoid 46 with a plunger 48 that is capable of extending from and retracting into the solenoid 46. The solenoid 46 may be positioned and oriented such that the solenoid 46 contacts one of the side walls of the car key slot 14 and is aligned with the opening on the side wall. The plunger 48 is seated in the opening of the side wall when it is retracted into the solenoid 46, as shown in FIG. 3. The plunger 48 protrudes in the interior of the car key slot 14 when it extends from the solenoid 46, as shown in FIG. 6.

Other embodiments of the locking mechanism 20 may include electromagnetic retainers. The electromagnetic retainers may include one or more inductors or coils of electrically conductive wire which generate a magnetic field when electric current flows through them. The magnetic field attracts the iron content of the car key 32, thereby retaining the car key 32 when the magnetic field is active.

In any embodiment, the locking mechanism 20 exists in one of either a first state or a second state. The first state is a locked state in which the locking mechanism 20 retains the car key 32. That is, in the first, locked state, the plunger 48 is extended from the solenoid 46, or electric current is flowing through the electromagnetic retainers so that a magnetic field is generated. The second state is an unlocked state in which the locking mechanism 20 releases, or at least does not retain, the car key 32. That is, in the second, unlocked state, the plunger 48 is retracted into the solenoid 46, or electric current is not flowing through the electromagnetic retainers and a magnetic field is not generated.

Generally, the locking mechanism 20 receives an electronic locking signal from the processing element 30 that determines whether the car key 32 should be retained or released. The locking signal may be an analog voltage whose level may vary to determine or control the state of the locking mechanism 20. Alternatively, the locking signal may be a digital voltage whose level may vary, or may be a stream of digital data whose value may vary, to determine or control the state of the locking mechanism 20.

In some embodiments, the locking mechanism 20 may retain or release the car key 32 according to a level or value of the locking signal. For example, the locking mechanism 20 may retain the car key 32, or exist in the locked state, when the locking signal has a first level or value, and the locking mechanism 20 may release the car key 32, or exist in the unlocked state, when the locking signal has a second level or value. In other embodiments, activation or presence of the locking signal causes the locking mechanism 20 to retain the car key 32, while deactivation or absence of the locking signal causes the locking mechanism 20 to release the car key 32.

The locking mechanism 20 is positioned within the internal cavity of the housing 12 adjacent to the bottom wall 36 and coupled to the car key slot 14.

The key detector 22 generally detects the presence of the car key 32 in the locking mechanism 20. The key detector 22 may include pressure sensors, proximity or contact switches, optical sensors, or the like, or combinations thereof. The key detector 22 may generate an electronic detection signal to indicate the presence or absence of the car key 32 in the car key slot 14. In some embodiments, the key detector 22 may generate the detection signal with a first analog electric voltage level or digital data value when the car key 32 is present in the car key slot 14, and may generate the detection signal with a second analog electric voltage level or digital data value when the car key 32 is absent from the car key slot 14. In other embodiments, the key detector 22 may generate the detection signal when the car key 32 is present in the locking mechanism 20, and may not generate the detection signal when the car key 32 is absent from the car key slot 14.

In some embodiments, the detection signal is communicated only to the locking mechanism 20 so that when the locking mechanism 20 receives the detection signal with the first level or value, it goes into the locked state and retains the car key 32. And, when the locking mechanism 20 receives the detection signal with the second level or value, it goes into the unlocked state and releases the car key 32. In other embodiments, the detection signal is communicated to the processing element 30.

The key detector 22 is positioned in the vicinity of the locking mechanism 20 and the car key slot 14.

The user interface 24 generally allows the user to utilize inputs and outputs to interact with the breathalyzer car key locking device 10. Inputs may include buttons, pushbuttons, knobs, keypads, or the like, or combinations thereof. Outputs may include audio speakers, lights, or the like, or combinations thereof. With the user interface 24, the user may be able to control the features and operation of the breathalyzer car key locking device 10. In exemplary embodiments, the user interface 24 is positioned on the front wall 42 of the housing 12.

The display 26 may include video devices of the following types: plasma, light-emitting diode (LED), organic LED (OLED), Light Emitting Polymer (LEP) or Polymer LED (PLED), liquid crystal display (LCD), thin film transistor (TFT) LCD, LED side-lit or back-lit LCD, or the like, or combinations thereof. The display 26 may include a screen on which information is presented, with the screen possessing a square or a rectangular aspect ratio that may be viewed in either a landscape or a portrait mode. The display 26 may be in electronic communication with the processing element 30 and may receive data or information therefrom that is to be shown on the display 26.

The communication element 28 generally allows the breathalyzer car key locking device 10 to communicate with computing devices, external systems, networks, and the like. The communication element 28 may include signal and/or data transmitting and receiving circuits, such as antennas, amplifiers, filters, mixers, oscillators, digital signal processors (DSPs), and the like. The communication element 28 may establish communication wirelessly by utilizing radio frequency (RF) signals and/or data that comply with communication standards such as cellular 2G, 3G, 4G, or 5G, Institute of Electrical and Electronics Engineers (IEEE) 802.11 standard such as WiFi, IEEE 802.16 standard such as WiMAX, Bluetooth™, or combinations thereof. In addition, the communication element 28 may utilize communication standards such as ANT, ANT+, Bluetooth™ low energy (BLE), the industrial, scientific, and medical (ISM) band at 2.4 gigahertz (GHz), or the like. Alternatively, or in addition, the communication element 28 may establish communication through connectors or couplers that receive metal conductor wires or cables which are compatible with networking technologies such as ethernet. The communication element 28 may be in electronic communication with the processing element 30.

The processing element 30 may comprise one or more processors. The processing element 30 may include electronic hardware components such as microprocessors (single-core or multi-core), microcontrollers, digital signal processors (DSPs), field-programmable gate arrays (FPGAs), analog and/or digital application-specific integrated circuits (ASICs), or the like, or combinations thereof. The processing element 30 may generally execute, process, or run instructions, code, code segments, code statements, software, firmware, programs, applications, apps, processes, services, daemons, or the like. The processing element 30 may also include hardware components such as registers, finite-state machines, sequential and combinational logic, and other electronic circuits that can perform the functions necessary for the operation of the current invention. In certain embodiments, the processing element 30 may include multiple computational components and functional blocks that are packaged separately but function as a single unit. The processing element 30 may be in electronic communication with the other electronic components through serial or parallel links that include universal busses, address busses, data busses, control lines, and the like.

The processing element 30 may further include, be embedded with, or be in electronic communication with, a memory element configured to store data in general, and digital or binary data in particular. The memory element may include exemplary electronic hardware data storage devices or components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. The memory element may include, or may constitute, a non-transitory "computer-readable medium". The memory element may store the instructions, code, code statements, code segments, software, firmware, programs, applications, apps, services, daemons, or the like that are executed by the processing element 30. The memory element may also store data that is received by the processing element 30 or the device in which the processing element 30 is implemented.

In addition, the processing element 30 may include, be embedded with, or be in electronic communication with, analog-to-digital converters (ADCs), digital-to-analog converters (DACs), amplifier circuits, filter circuits, or the like, or combinations thereof.

The processing element 30 may be operable, configured, or programmed to perform the following functions by utilizing hardware, software, firmware, or combinations thereof. The processing element 30 receives input data or signals from the user interface 24 as the user operates the breathalyzer car key locking device 10 to either initiate retaining the car key 32 or start the breath analysis process.

The processing element 30 also receives the alcohol level signal from the alcohol sensor 18 during the breath analysis process. The alcohol level signal may include an analog voltage, which is converted to digital data by a DAC, or the alcohol level signal may include digital data, which does not need to be converted. The processing element 30 may receive the alcohol level signal multiple times or may sample and hold the value of the alcohol level signal multiple times within a short period of time. The processing element 30 may determine or calculate an average of the multiple alcohol level signal readings, which is considered the blood alcohol level.

The processing element 30 may also receive the electronic signal or digital data from one or more additional or alternative sensors configured to detect the presence of marijuana or THC markers in the user's body. The electronic signal or digital data may include a level or value that varies according to the amount of the markers detected.

The processing element 30 receives input data from the communication element 28. The data is typically from an accompanying smartphone app.

The processing element 30 may receive the detection signal from the key detector 22.

The processing element 30 transmits data to the communication element 28 that is transferred to the smartphone app. The data may include the blood alcohol level, among others.

The processing element 30 transmits data to the display 26 to be shown to the user. The data may include prompts to have the user perform the breath analysis process and readings of the measured blood alcohol level.

The processing element 30 transmits the locking signal to the locking mechanism 20. As discussed above, the locking signal may include an analog electric voltage level or a digital data value. In some embodiments, the processing element 30 may transmit the locking signal with a first level or value when the car key 32 should be retained or locked, and a second level or value when the car key 32 should be released or unlocked. In other embodiments, the processing element 30 may transmit the locking signal only when the locking mechanism 20 should retain the car key 32.

The processing element 30 may be programmed to perform the following steps. The processing element 30 may transmit data to the display to be shown to the user that includes a message prompting the user to enter a blood alcohol level threshold, below which he wants the breathalyzer car key locking device 10 to release the car key 32. The processing element 30 receives the data from the user interface 24 that includes the threshold. The processing element 30 then transmits the locking signal with the first level or value to the locking mechanism 20. The processing element 30 may transmit data to the display which indicates that the key is being retained. When the user wants to perform a breath analysis process, he presses a key on the user interface 24. The processing element 30 receives the data or signal from the user interface 24 and starts a countdown timer, the value of which is also transmitted to the display to be shown to the user. The timer may start at a value of 5, for example, and count down to 0. When the value reaches 0, the user should blow into the mouthpiece 16. The processing element 30 then receives levels or data from the alcohol sensor 18, converts the levels to digital data if necessary, and may, if multiple readings are received, average the data from the alcohol sensor 18. If the single reading, or the average of the readings, which is the blood alcohol level of the user, has a value that is above or equal to the blood alcohol level threshold, then the processing element 30 may transmit data to the display 26 that shows the blood alcohol level and/or lets the user know that he failed the test and will now have to wait. The processing element 30 may also set the countdown timer for a period of time for the user to wait before he can try to analyze his breath again. The period of time for waiting may be set during production or may be adjustable to be greater than a certain minimum time period. The time period for waiting may range from a minimum time, as an example, of approximately 20 minutes to, as an example, approximately 1 hour. During the waiting time period, the processing element 30 is still transmitting the locking signal to the locking mechanism 20 to maintain the locked state. Furthermore, the processing element 30 does not accept any data from the alcohol sensor 18.

After waiting for the waiting time period for a first time, the user may try to analyze his breath for a second time. As with the first time, he presses a key on the user interface 24. The processing element 30 receives the data or signal from the user interface 24 and starts the countdown timer, the value of which is also transmitted to the display to be shown to the user. At the termination of the count, the user blows into the mouthpiece 16 and the processing element 30 receives levels or data from the alcohol sensor 18. If the single reading, or the average of the readings, has a value that is above or equal to the blood alcohol level threshold, then the processing element 30 transmits messages to the display 26 and starts the countdown timer for the waiting time period. During the waiting time period, the processing element 30 is still transmitting the locking signal to the locking mechanism 20 to maintain the locked state. Furthermore, the processing element 30 does not accept any data from the alcohol sensor 18.

Upon waiting for the waiting time period for a second time, the user may try to analyze his breath for a third time. After repeating the process described above, if the single reading, or the average of the readings, has a value that is above or equal to the blood alcohol level threshold, then the processing element 30 transmits data to the display 26 which displays the blood alcohol level and/or informs the user that he has failed the test a third time. The processing element 30 may also transmit data to the display 26 to advise the user to call for other transportation, such as a taxi, a ride sharing service, or a friend. Additionally, or alternatively, the processing element 30 may transmit data to the communication element 28 which transmits the data to the accompanying app running on the user's smartphone to instruct the app to automatically call or text message a taxi, a ride sharing service, or a friend.

If, after the first, second, or third time the user blows into the mouthpiece 16 for the alcohol sensor 18 to measure the user's blood alcohol level, the blood alcohol level measurement is below the blood alcohol level threshold, then the processing element 30 transmits the locking signal with the second level or value to the locking mechanism 20. This unlocks or releases the car key 32.

In certain embodiments, the processing element 30 receives the detection signal from the key detector 22, which indicates the presence or absence of the car key 32 in the car key slot 14. Typically, while the locking mechanism 20 is in the locked state, the key detector 22 transmits the detection signal with the first level or value to the processing element 30 to indicate that the car key 32 is in the car key slot 14. If the locking mechanism 20 is supposed to be in the locked state and the key detector 22 transmits the detection signal with the second level or value, which indicates that the car key 32 is no longer in the car key slot 14, then it is at least possible that the breathalyzer car key locking device 10 has been tampered with and/or the car key 32 has been removed from the breathalyzer car key locking device 10 prematurely. In this case, the processing element 30 transmits data to the communication element 28 which transmits the data to the accompanying app running on the user's smartphone to instruct the app to automatically call law enforcement.

In some embodiments, the device 10 may be utilized to detect the presence of marijuana or THC markers in the user's body. The processing element 30 may receive the electronic signal or digital data from one or more additional or alternative sensors. The electronic signal or digital data may include levels or values that vary according to the amount of the markers detected. The processing element 30 may then process and analyze the levels or values in a similar fashion to the blood alcohol level signal as described above. For example, the processing element 30 may compare the levels or values to thresholds and release the car key 32 or begin the waiting process, as discussed above, according to whether the levels or values are above the thresholds or below them. In addition, the processing element 30 may repeat the waiting process as necessary.

The breathalyzer car key locking device 10 may operate as follows. The user may optionally set up the accompanying smartphone app before using the breathalyzer car key locking device 10. The set up may include entering the name and phone number of at least one friend who would be willing to drive the user home, or to another destination, if the user does not pass the breath analysis test for three times. The set up may also include registering and/or pairing the breathalyzer car key locking device 10 and the smartphone to ensure wireless communication between the two. After the setup is complete, the user utilizes the user interface 24 to start the process of having the breathalyzer car key locking device 10 retain his car key 32. The user may enter a blood alcohol level threshold or may accept a preprogrammed default value. Exemplary blood alcohol level threshold values may range from 0.02% to 0.07%. The user then inserts the car key 32 into the car key slot 14. The key detector 22 senses the presence of the car key 32 in the car key slot 14 and transmits the detection signal indicating that the car key 32 is present. The processing element 30 receives the detection signal indicating that the car key 32 is present and in turn transmits the locking signal to the locking mechanism 20 to retain the car key 32. The user may then proceed to his social events or engagements where alcohol will be served and may consume alcohol.

When the user wants to retrieve his car key 32 in order to drive his car, he utilizes the user interface 24 to start the breath analysis process. Following prompts from the display 26, he breathes or blows into the mouthpiece 16 at least one time. The alcohol sensor 18 determines the blood alcohol level, which may be shown on the display 26. If the blood alcohol level is greater than or equal to the blood alcohol level threshold, then the breathalyzer car key locking device 10 retains the car key 32 and shows a message on the display 26 that the user has failed the test and/or he will have to wait for a period of time before attempting the breath analysis process again. If the blood alcohol level is less than the blood alcohol level threshold, then the breathalyzer car key locking device 10 releases the car key 32 so that the user may retrieve it and drive his car.

If the user failed the first test and has waited for the time period, then he utilizes the user interface 24 to initiate the breath analysis process again. Following prompts from the display 26, he breathes or blows into the mouthpiece 16 at least one time. The alcohol sensor 18 determines the blood alcohol level. If the blood alcohol level is greater than or equal to the blood alcohol level threshold, then the breathalyzer car key locking device 10 continues to retain the car key 32 and shows a message on the display 26 that the user has failed the test and/or he will have to wait before attempting the breath analysis process again. If the blood alcohol level is less than the blood alcohol level threshold, then the breathalyzer car key locking device 10 releases the car key 32.

If the user failed the second test and has waited for the time period again, then he utilizes the user interface 24 to initiate the breath analysis process for a third time. He breathes or blows into the mouthpiece 16 at least one time, and the alcohol sensor 18 determines the blood alcohol level. If the blood alcohol level is greater than or equal to the blood alcohol level threshold, then the breathalyzer car key locking device 10 continues to retain the car key 32 and shows a message on the display 26 that the user has failed the test. The breathalyzer car key locking device 10 may then send a message or data to the accompanying app on the user's smartphone, which may instruct the app to automatically call or text message a taxi, a ride sharing service, or a friend. If the blood alcohol level is less than the blood alcohol level threshold, then the breathalyzer car key locking device 10 releases the car key 32.

Figure 7:
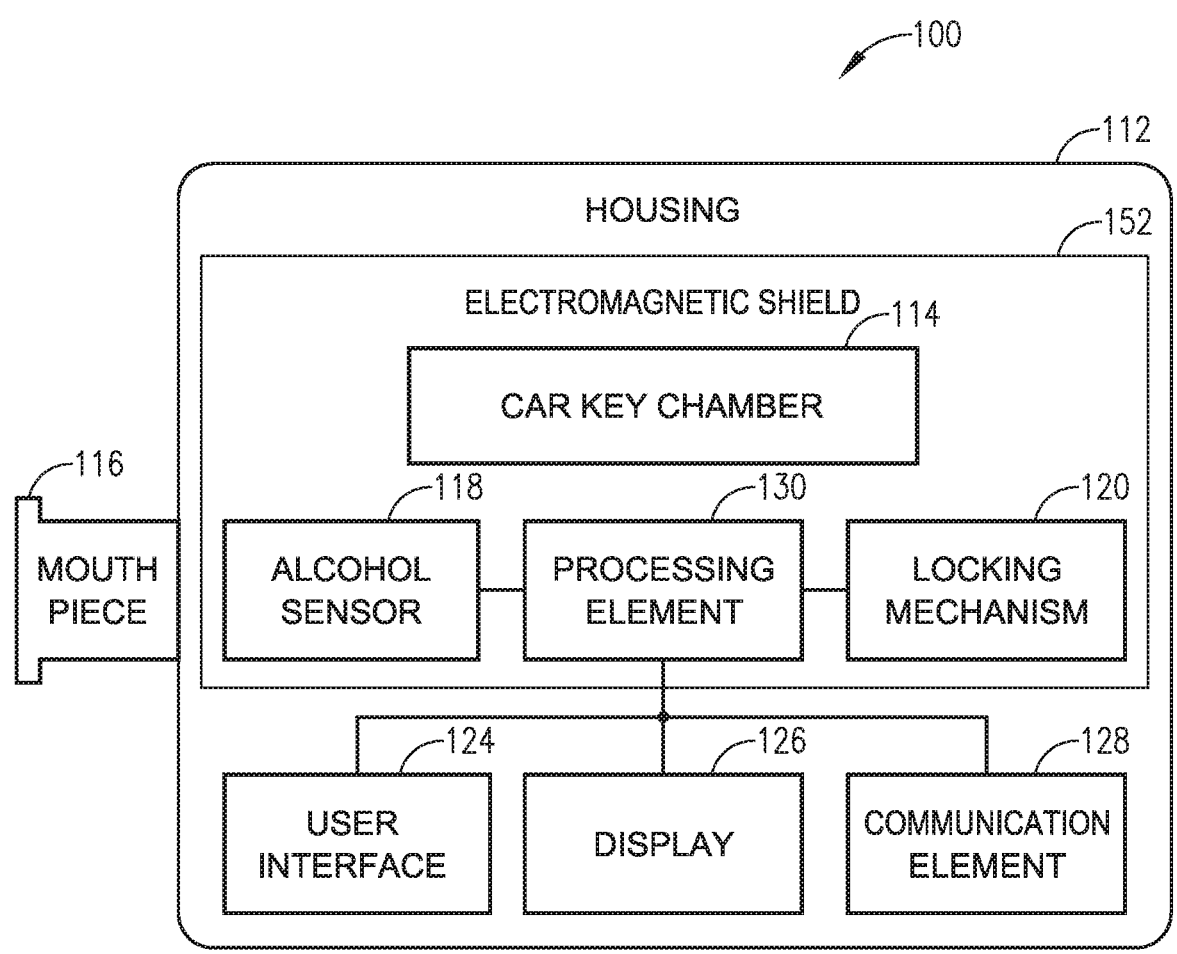
FIG. 7 is a schematic block diagram of a second embodiment of the breathalyzer car key locking device.

A second embodiment of the breathalyzer car key locking device 100 is shown in FIG. 7 and is generally utilized with car keys which include a wireless, RF transmitter and receiver (transceiver) that communicates with a vehicle—commonly known as a "fob", although the breathalyzer car key locking device 100 may also be utilized with traditional car keys that do not include a transceiver. The breathalyzer car key locking device 100 broadly comprises a housing 112, a mouthpiece 116, an alcohol sensor 118, a locking mechanism 120, a user interface 124, a display 126, a communication element 128, and a processing element 130. The mouthpiece 116, the alcohol sensor 118, the locking mechanism 120, the user interface 124, the display 126, the communication element 128, and the processing element 130 may each have a similar structure, operation, and function as the like-named components discussed above for the breathalyzer car key locking device 10. The breathalyzer car key locking device 100 may further comprise car key chamber 114 and an electromagnetic shield 152.

The housing 112 retains the other components of the breathalyzer car key locking mechanism 120. The housing 12 may include a plurality of walls connected to one another to form a box with an internal cavity. One or more of the walls may be hinged or slidable or may otherwise open in order to provide access into the internal cavity. In certain embodiments, the housing 112, or a portion of the housing 112, may include a clamshell structure or may have a clamshell shape. The mouthpiece 116, the user interface 124, and the display 126 may be positioned on, or accessed on, an exterior of one of the walls of the housing 112.

The car key chamber 114 retains the car key fob until the user passes the breath analysis test. The car key chamber 114 may exist in one of two states including an open state and a closed state. The car key chamber 114 is positioned within the internal cavity of the housing 112 and may be defined by a plurality of the walls of the housing 112. The car key chamber 114 may be accessed by opening, sliding, or moving one or more of the walls, or portions of one or more of the walls, of the housing 112. When one or more of the walls are open, or able to be opened, to provide access, then the car key chamber 114 is in the open state. When the walls are closed denying access, the car key chamber 114 is in the closed state.

The car key chamber 114 may include latching or locking components that interface with the locking mechanism 120 such that the plunger of the locking mechanism 120 solenoid engages the latching or locking components. For example, a first wall of the housing 112 may include a first latching or locking component, while a second wall, adjacent to the first wall, may include a second latching or locking component. The first wall may be movable or slidable and may contact the second wall when the car key chamber 114 is closed such that an opening on the first latching or locking component aligns with, or overlaps, an opening on the second latching or locking component. The plunger of the locking mechanism 120 solenoid may extend and pass through the openings of the two latching or locking components—thereby preventing the latching or locking components from moving. Thus, the locked state of the locking mechanism 120 (with the plunger extended) corresponds to the closed state of the car key chamber 114, while the unlocked state of the locking mechanism 120 (with the plunger retracted) corresponds to the open state of the car key chamber 114. There are other configurations of the car key chamber 114 and the locking mechanism 120 that fall within the scope of the current invention.

The electromagnetic shield 152 generally prevents wireless, RF communication between the car key fob when it is within the closed car key chamber 114 and electronic devices outside of the breathalyzer car key locking device 100. The electromagnetic shield 152 may be formed from structures such as a Faraday cage or similar structures of electrically conductive mesh or sheeting. The electromagnetic shield 152 may be attached to, embedded in, or otherwise integrated with, a plurality of the walls of the housing 112. The electromagnetic shield 152 may be structured such that it completely encloses the car key chamber 114 (when it is closed), the alcohol sensor 118, the locking mechanism 120, and the processing element 130. The user interface 124, the display 126, and the communication element 128 are positioned outside of the electromagnetic shield 152.

The breathalyzer car key locking device 100 may operate as follows. Assuming that the user has set up the accompanying smartphone app as described above, he utilizes the user interface 124 to start the process of having the breathalyzer car key locking device 100 retain his car key fob. The user may enter a blood alcohol level threshold or may accept a preprogrammed default value. The user then opens, slides, or moves one or more walls of the housing 112 to access the car key chamber 114 so that it is in the open state. The user places his car key fob in the car key chamber 114 and closes, slides, or moves the walls so that the car key chamber 114 is in the closed state. The user may utilize the user interface 124 to let the processing element 130 know that the car key chamber 114 is closed with the car key fob inside. The processing element 130 then transmits the locking signal to the locking mechanism 120 to place it in the locked state to prevent opening of the car key chamber 114. While the car key chamber 114 is closed, the electromagnetic shield 152 prevents wireless, RF communication between the car key fob and other electronic devices, such as vehicle operating systems. The user may then proceed to his social events or engagements where alcohol will be served and may consume alcohol.

The operation of the breathalyzer car key locking device 100 then proceeds much the same as described above. When the user wants to retrieve his car key fob in order to drive his car, he utilizes the user interface 124 to start the breath analysis process. Following prompts from the display 126, he breathes or blows into the mouthpiece 116 at least one time. The alcohol sensor 118 determines the blood alcohol level. If the blood alcohol level is greater than or equal to the blood alcohol level threshold, then the breathalyzer car key locking device 100 retains the car key fob within the car key chamber 114 and shows a message on the display 126 that the user has failed the test and/or he will have to wait for a period of time before attempting the breath analysis process again. If the blood alcohol level is less than the blood alcohol level threshold, then the processing element 130 transmits the locking signal to the locking mechanism 120 to change to the unlocked state so that the user may open the car key chamber 114, retrieve his car key fob, and drive his car.

If the user failed the first test and has waited for the time period, then he utilizes the user interface 124 to initiate the breath analysis process again. Following prompts from the display 126, he breathes or blows into the mouthpiece 116 at least one time. The alcohol sensor 118 determines the blood alcohol level. If the blood alcohol level is greater than or equal to the blood alcohol level threshold, then the breathalyzer car key locking device 100 continues to retain the car key fob and shows a message on the display 126 that the user has failed the test and/or he will have to wait before attempting the breath analysis process again. If the blood alcohol level is less than the blood alcohol level threshold, then the locking mechanism 120 is changed to the unlocked state so that the user may open the car key chamber 114, retrieve his car key fob, and drive his car.

If the user failed the second test and has waited for the time period again, then he utilizes the user interface 124 to initiate the breath analysis process for a third time. He breathes or blows into the mouthpiece 116 at least one time, and the alcohol sensor 118 determines the blood alcohol level. If the blood alcohol level is greater than or equal to the blood alcohol level threshold, then the breathalyzer car key locking device 100 continues to retain the car key fob and shows a message on the display 126 that the user has failed the test. The breathalyzer car key locking device 100 may then send a message or data to the accompanying app on the user's smartphone, which may instruct the app to automatically call or text message a taxi, a ride sharing service, or a friend. If the blood alcohol level is less than the blood alcohol level threshold, then the locking mechanism 120 is changed to the unlocked state so that the user may open the car key chamber 114, retrieve his car key fob, and drive his car.

Additional Considerations

Throughout this specification, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current invention can include a variety of combinations and/or integrations of the embodiments described herein.

Although the present application sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as computer hardware that operates to perform certain operations as described herein.

In various embodiments, computer hardware, such as a processing element, may be implemented as special purpose or as general purpose. For example, the processing element may comprise dedicated circuitry or logic that is permanently configured, such as an application-specific integrated circuit (ASIC), or indefinitely configured, such as an FPGA, to perform certain operations. The processing element may also comprise programmable logic or circuitry (e.g., as encompassed within a general-purpose processor or other programmable processor) that is temporarily configured by software to perform certain operations. It will be appreciated that the decision to implement the processing element as special purpose, in dedicated and permanently configured circuitry, or as general purpose (e.g., configured by software) may be driven by cost and time considerations.

Accordingly, the term "processing element" or equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processing element is temporarily configured (e.g., programmed), each of the processing elements need not be configured or instantiated at any one instance in time. For example, where the processing element comprises a general-purpose processor configured using software, the general-purpose processor may be configured as respective different processing elements at different times. Software may accordingly configure the processing element to constitute a particular hardware configuration at one instance of time and to constitute a different hardware configuration at a different instance of time.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at different times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, at a later time, access the memory device to retrieve and process the stored output. Computer hardware components may also initiate communications with input or output devices, and may operate on a resource (e.g., a collection of information).

The various operations of example methods described herein may be performed, at least partially, by one or more processing elements that are temporarily configured (e.g., by software) or permanently configured to perform the relevant operations. Whether temporarily or permanently configured, such processing elements may constitute processing element-implemented modules that operate to perform one or more operations or functions. The modules referred to herein may, in some example embodiments, comprise processing element-implemented modules.

Similarly, the methods or routines described herein may be at least partially processing element-implemented. For example, at least some of the operations of a method may be performed by one or more processing elements or processing element-implemented hardware modules. The performance of certain of the operations may be distributed among the one or more processing elements, not only residing within a single machine, but deployed across a number of machines. In some example embodiments, the processing elements may be located in a single location (e.g., within a home environment, an office environment or as a server farm), while in other embodiments the processing elements may be distributed across a number of locations.

Unless specifically stated otherwise, discussions herein using words such as "processing," "computing," "calculating," "determining," "presenting," "displaying," or the like may refer to actions or processes of a machine (e.g., a computer with a processing element and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The patent claims at the end of this patent application are not intended to be construed under 35 U.S.C. § 112(f) unless traditional means-plus-function language is expressly recited, such as "means for" or "step for" language being explicitly recited in the claim(s).

Although the technology has been described with reference to the embodiments illustrated in the attached drawing figures, it is noted that equivalents may be employed and substitutions made herein without departing from the scope of the technology as recited in the claims.

Having thus described various embodiments of the technology, what is claimed as new and desired to be protected by Letters Patent includes the following:

1. A breathalyzer car key locking device comprising:
    a housing including a plurality of walls connected to one another to form a box with an internal cavity;
    a mouthpiece coupled to the housing and configured to receive breath from a user during a breath test;
    an alcohol sensor positioned in the internal cavity and configured to, for each breath test, receive the user's breath from the mouthpiece, determine a blood alcohol level of the breath, and output an electronic blood alcohol level signal whose voltage level or digital data value varies according to the determined blood alcohol level;
    a locking mechanism positioned in the internal cavity and existing in one of two states including a locked state and an unlocked state, the locking mechanism configured to retain a car key in the locked state and release the car key in the unlocked state; and
    a processing element configured or programmed to
        receive the blood alcohol level signal from the alcohol sensor for each breath test,
        transmit an electronic locking signal for each breath test to the locking mechanism that places the locking mechanism in the locked state when the voltage level or digital data value of the blood alcohol level signal is greater than or equal to a predetermined threshold and places the locking mechanism in the unlocked state when the voltage level or digital data value of the blood alcohol level signal is less than the threshold, and
        transmit instructions through a communication element to an application executed on a smartphone of the user to contact a third party for transportation after receiving the blood alcohol level signal for a fixed number of consecutive breath tests in which the blood alcohol level signal is greater than or equal to the threshold.

2. The breathalyzer car key locking device of claim 1, further comprising a car key slot accessed through an opening in a wall of the housing, the car key slot configured to receive the car key, the car key slot including a plurality of walls connected to one another to form an open-ended box, one of the walls including an opening through which the locking mechanism contacts the car key when in the locked state.

3. The breathalyzer car key locking device of claim 1, wherein the locking mechanism includes a solenoid with a plunger configured to extend from the solenoid when the locking mechanism is in the locked state and retract into the solenoid when the locking mechanism is in the unlocked state.

4. The breathalyzer car key locking device of claim 1, wherein
    the locking mechanism includes a solenoid with a plunger configured to extend from the solenoid when the locking mechanism is in the locked state and retract into the solenoid when the locking mechanism is in the unlocked state; and
    the breathalyzer car key locking device further comprises a car key slot accessed through an opening in a wall of the housing, the car key slot configured to receive the car key, the car key slot including a plurality of walls connected to one another to form an open-ended box, one of the walls including an opening which receives the plunger such that the plunger contacts the car key when the locking mechanism is in the locked state and does not contact the car key when the locking mechanism is in the unlocked state.

5. The breathalyzer car key locking device of claim 1, wherein the processing element is further configured or programmed to transmit the locking signal to the locking mechanism to place the locking mechanism in the locked state when the user first engages the breathalyzer car key locking device to retain the car key.

6. The breathalyzer car key locking device of claim 1, wherein the processing element is further configured or programmed to
receive a plurality of readings of the blood alcohol level signal from the alcohol sensor, and
calculate an average of the readings to compare to the threshold.

7. The breathalyzer car key locking device of claim 1, wherein the processing element is further configured or programmed to
alert the user that his blood alcohol level is above the threshold when the voltage level or digital data value of the blood alcohol level signal is greater than or equal to the threshold,
wait for a first period of time before allowing the user to breathe into the mouthpiece again when the voltage level or digital data value of the blood alcohol level signal is greater than or equal to the threshold, and
transmit the locking signal to the locking mechanism to place the locking mechanism in the locked state during the first period of time.

8. The breathalyzer car key locking device of claim 7, wherein the processing element is further configured or programmed to
receive the blood alcohol level signal from the alcohol sensor after waiting for the first period of time,
transmit the locking signal to the locking mechanism to place the locking mechanism in the locked state when the voltage level or digital data value of the blood alcohol level signal is greater than or equal to the threshold and place the locking mechanism in the unlocked state when the voltage level or digital data value of the blood alcohol level signal is less than the threshold,
alert the user that his blood alcohol level is above the threshold when the voltage level or digital data value of the blood alcohol level signal is greater than or equal to the threshold, and
wait for a second period of time before allowing the user to breathe into the mouthpiece again when the voltage level or digital data value of the blood alcohol level signal is greater than or equal to the threshold.

9. The breathalyzer car key locking device of claim 8, wherein the processing element is further configured or programmed to
receive the blood alcohol level signal from the alcohol sensor after waiting for the second period of time,
transmit the locking signal to the locking mechanism to place the locking mechanism in the locked state when the voltage level or digital data value of the blood alcohol level signal is greater than or equal to the threshold and place the locking mechanism in the unlocked state when the voltage level or digital data value of the blood alcohol level signal is less than the threshold,
alert the user that his blood alcohol level is above the threshold when the voltage level or digital data value of the blood alcohol level signal is greater than or equal to the threshold, and
transmit instructions through a communication element to an application executed on the user's smartphone to contact a taxi, a ride sharing service, or a friend.

10. A breathalyzer car key locking device comprising:
a housing including a plurality of walls connected to one another to form a box with an internal cavity;
a mouthpiece coupled to the housing and configured to receive breath from a user during a breath test;
an alcohol sensor positioned in the internal cavity and configured to, for each breath test, receive the user's breath from the mouthpiece, determine a blood alcohol level of the breath, and output an electronic blood alcohol level signal whose voltage level or digital data value varies according to the determined blood alcohol level;
a locking mechanism positioned in the internal cavity and existing in one of two states including a locked state and an unlocked state, the locking mechanism including a solenoid with a plunger configured to extend from the solenoid when in the locked state and retract into the solenoid when in the unlocked state;
a car key slot accessed through an opening in a wall of the housing, the car key slot configured to receive a car key, the car key slot including a plurality of walls connected to one another to form an open-ended box, one of the walls including an opening which receives the plunger such that the plunger contacts the car key to retain the car key when in the locked state and does not contact the car key to release the car key when in the unlocked state; and
a processing element configured or programmed to
receive the blood alcohol level signal from the alcohol sensor for each breath test,
transmit an electronic locking signal for each breath test to the locking mechanism that places the locking mechanism in the locked state when the voltage level or digital data value of the blood alcohol level signal is greater than or equal to a predetermined threshold and places the locking mechanism in the unlocked state when the voltage level or digital data value of the blood alcohol level signal is less than the threshold, and
transmit instructions through a communication element to an application executed on a smartphone of the user to contact a third party for transportation after receiving the blood alcohol level signal for a fixed number of consecutive breath tests in which the blood alcohol level signal is greater than or equal to the threshold.

11. The breathalyzer car key locking device of claim 10, wherein the processing element is further configured or programmed to transmit the locking signal to the locking mechanism to place the locking mechanism in the locked state when the user first engages the breathalyzer car key locking device to retain the car key.

12. The breathalyzer car key locking device of claim 10, wherein the processing element is further configured or programmed to
receive a plurality of readings of the blood alcohol level signal from the alcohol sensor, and
calculate an average of the readings to compare to the threshold.

13. The breathalyzer car key locking device of claim 10, wherein the processing element is further configured or programmed to
- alert the user that his blood alcohol level is above the threshold when the voltage level or digital data value of the blood alcohol level signal is greater than or equal to the threshold,
- wait for a first period of time before allowing the user to breathe into the mouthpiece again when the voltage level or digital data value of the blood alcohol level signal is greater than or equal to the threshold, and
- transmit the locking signal to the locking mechanism to place the locking mechanism in the locked state during the first period of time.

14. The breathalyzer car key locking device of claim 13, wherein the processing element is further configured or programmed to
- receive the blood alcohol level signal from the alcohol sensor after waiting for the first period of time,
- transmit the locking signal to the locking mechanism to place the locking mechanism in the locked state when the voltage level or digital data value of the blood alcohol level signal is greater than or equal to the threshold and place the locking mechanism in the unlocked state when the voltage level or digital data value of the blood alcohol level signal is less than the threshold,
- alert the user that his blood alcohol level is above the threshold when the voltage level or digital data value of the blood alcohol level signal is greater than or equal to the threshold, and
- wait for a second period of time before allowing the user to breathe into the mouthpiece again when the voltage level or digital data value of the blood alcohol level signal is greater than or equal to the threshold.

15. The breathalyzer car key locking device of claim 14, wherein the processing element is further configured or programmed to
- receive the blood alcohol level signal from the alcohol sensor after waiting for the second period of time,
- transmit the locking signal to the locking mechanism to place the locking mechanism in the locked state when the voltage level or digital data value of the blood alcohol level signal is greater than or equal to the threshold and place the locking mechanism in the unlocked state when the voltage level or digital data value of the blood alcohol level signal is less than the threshold,
- alert the user that his blood alcohol level is above the threshold when the voltage level or digital data value of the blood alcohol level signal is greater than or equal to the threshold, and
- transmit instructions through a communication element to an application executed on the user's smartphone to contact a taxi, a ride sharing service, or a friend.

16. A breathalyzer car key locking device comprising:
- a housing including a plurality of walls connected to one another to form a box with an internal cavity;
- a mouthpiece coupled to the housing and configured to receive breath from a user during a breath test;
- an alcohol sensor positioned in the internal cavity and configured to, for each breath test, receive the user's breath from the mouthpiece, determine a blood alcohol level of the breath, and output an electronic blood alcohol level signal whose voltage level or digital data value varies according to the determined blood alcohol level;
- a car key chamber positioned in the internal cavity and configured to retain a car key, the car key chamber existing in one of two states including an open state and a closed state;
- a locking mechanism positioned in the internal cavity and existing in one of two states including a locked state and an unlocked state, the locking mechanism configured to prevent access to the car key chamber in the locked state and allow access to the car key chamber in the unlocked state;
- a processing element configured or programmed to
  - receive the blood alcohol level signal from the alcohol sensor for each breath test,
  - transmit an electronic locking signal for each breath test to the locking mechanism that places the locking mechanism in the locked state when the voltage level or digital data value of the blood alcohol level signal is greater than or equal to a predetermined threshold and places the locking mechanism in the unlocked state when the voltage level or digital data value of the blood alcohol level signal is less than the threshold, and
  - transmit instructions through a communication element to an application executed on a smartphone of the user to contact a third party for transportation after receiving the blood alcohol level signal for a fixed number of consecutive breath tests in which the blood alcohol level signal is greater than or equal to the threshold.

17. The breathalyzer car key locking device of claim 16, further comprising an electromagnetic shield integrated with the housing such that the electromagnetic shield encloses the car key chamber when the car key chamber is in the closed state, the electromagnetic shield configured to prevent wireless, radio frequency communication between the car key when it is within the car key chamber and electronic devices outside of the breathalyzer car key locking device.

18. The breathalyzer car key locking device of claim 16, wherein the car key chamber is in the open state when it can be accessed by opening, sliding, or moving one or more of the walls, or portions of one or more of the walls, of the housing and the car key chamber is in the closed state when one or more of the walls, or portions of one or more of the walls, of the housing cannot be opened, slid, or moved to access the car key chamber.

19. The breathalyzer car key locking device of claim 18, wherein the processing element is further configured or programmed to transmit the locking signal to the locking mechanism to place the locking mechanism in the locked state when the user first engages the breathalyzer car key locking device to retain the car key.

20. The breathalyzer car key locking device of claim 18, wherein the processing element is further configured or programmed to
- alert the user that his blood alcohol level is above the threshold when the voltage level or digital data value of the blood alcohol level signal is greater than or equal to the threshold,
- wait for a first period of time before allowing the user to breathe into the mouthpiece again when the voltage level or digital data value of the blood alcohol level signal is greater than or equal to the threshold, and
- transmit the locking signal to the locking mechanism to place the locking mechanism in the locked state during the first period of time.

* * * * *